United States Patent [19]

Spry

[11] Patent Number: 4,756,618

[45] Date of Patent: Jul. 12, 1988

[54] REFRACTIVE INDEX MEASUREMENT CELL

[76] Inventor: Robert J. Spry, 5830 South Worley Rd., Tipp City, Ohio 45371

[21] Appl. No.: 73,614

[22] Filed: Jul. 15, 1987

[51] Int. Cl.$^4$ .............................................. G01N 21/41
[52] U.S. Cl. .................................... 356/134; 356/130; 356/246
[58] Field of Search ............... 356/128, 130, 131, 132, 356/134, 135, 136, 246

[56] References Cited

U.S. PATENT DOCUMENTS

| | | | |
|---|---|---|---|
| 3,450,476 | 6/1969 | Rando | 356/134 |
| 3,636,360 | 1/1972 | Oishi et al. | 356/134 |
| 3,797,940 | 3/1974 | King | 356/134 |

OTHER PUBLICATIONS

Physics/Chemistry Catalog 1983/1984, Central Scientific Company, Franklin Park, Ill. p. 135.

*Primary Examiner*—F. L. Evans
*Attorney, Agent, or Firm*—Bobby D. Scearce; Donald J. Singer

[57] ABSTRACT

A refractive index measurement cell for liquid samples and method for measuring refractive indices of liquids are described which comprise a transparent tubular member closed at one end defining a sample volume of semicylindrical shape with respect to an axis for containing a liquid and having a diametrically disposed wall element including a flat surface defining the sample volume and containing the axis; a reference line coincident with the axis on the flat surface; a light source for projecting a light beam through the wall element, reference line and sample volume, whereby the beam is refracted at the flat surface; and a detector, selectively positionable about the axis of the tubular member, for detecting the light beam transmitted through the sample volume and for measuring the angular position of the beam about the axis.

7 Claims, 1 Drawing Sheet

U.S. Patent    Jul. 12, 1988    4,756,618

REFRACTIVE INDEX MEASUREMENT CELL

RIGHTS OF THE GOVERNMENT

The invention described herein may be manufactured and used by or for the Government of the United States for all governmental purposes without the payment of any royalty.

BACKGROUND OF THE INVENTION

The present invention relates generally to devices for measurement of refractive indices of fluid media, and more particularly to a practical laboratory instrument for precision measurement of the refractive index of a liquid.

The invention is a light transmissive refractive index measurement cell for liquid samples and comprises a transparent hollow cylindrical section closed at one end with a transparent flat wall element disposed transversely of the cylindrical section; one surface of the wall element includes a reference line coincident with the axis of the cylindrical section and together with the inner surface of the cylindrical section defines a sample volume of semicylindrical shape. With the sample volume empty, a light beam is projected from a source through the wall element, reference line and sample volume to a detector opposite the source to establish an angle of refraction through the empty cell. The sample volume is then filled with liquid and the angle of refraction is remeasured. The refractive index of the liquid is calculated using Snell's law.

The refractive index measurement cell of the invention may be used for rapid and accurate measurement of the refractive indices of various liquids, including liquids having intensity dependent nonlinear indices. In the observation of the beam, the refracted path of the beam is defined from the detector to the reference line through the sample volume along a radius of the semicylindrical section; no refraction occurs in the cylindrical wall of the cell, and angle measurements for the refracted beam are independent of the refractive indices of materials of construction of the cell. Residual errors are neither present in the measurements nor need be accounted for because of dimensions of component parts.

It is therefore a principal object of the invention to provide a refractive index measurement cell for liquid samples.

It is a further object to provide a laboratory device for straightforward measurement of refractive indices of liquids.

It is yet a further object to provide a device for rapid and accurate measurement of non-linear refractive indices of liquids.

These and other objects of the invention will become apparent as the detailed description of representative embodiments proceeds.

SUMMARY OF THE INVENTION

In accordance with the foregoing principles and objects of the invention, a refractive index measurement cell for liquid samples and method for measuring refractive indices comprise a transparent tubular member closed at one end defining a sample volume of semicylindrical shape with respect to an axis for containing a liquid and having a diametrically disposed wall element including a flat surface defining the sample volume and containing the axis; a reference line coincident with the axis on the flat surface; a light source for projecting a light beam through the wall element, reference line and sample volume, whereby the beam is refracted at the flat surface; and a detector selectively positionable about the axis of the tubular member for detecting the light beam transmitted through the sample volume and for measuring the angular position of the beam about the axis.

DESCRIPTION OF THE DRAWINGS

The invention will be clearly understood from the following detailed description of representative embodiments thereof read in conjunction with the accompanying drawings wherein.

DETAILED DESCRIPTION

Figure 1:
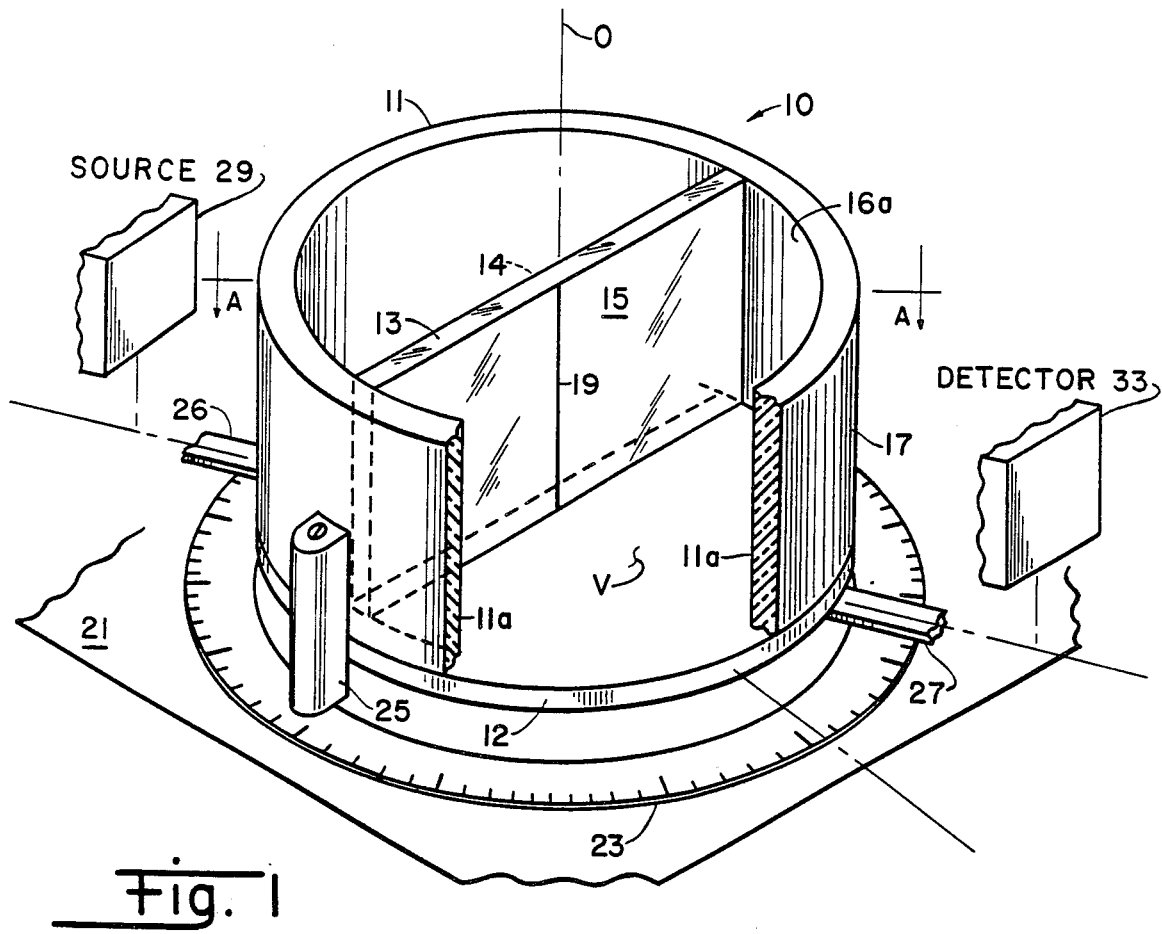
FIG. 1 is an isometric view in partial cutaway of a representative configuration for the refractive index measurement cell of the invention.

Referring now to the drawinqs, shown in FIG. 1 is an isometric view of a representative arrangement for the refractive index cell 10 of the invention. Cell 10 comprises a transparent cylinder 11 of glass, quartz, plexiglass, plastic, or other suitable material as would occur to one skilled in the art guided by these teachings. Cylinder 11 has an axis of symmetry O and may have substantially any convenient outside diameter, inside diameter, wall thickness or length so long as it is substantially precise in curvature and uniform in wall thickness. For example, a workable cell 10 may be constructed substantially to the scale of FIG. 1 (i.e. about 4 inches in diameter by about 1.5 inches high). Floor 12 of appropriate shape supports cylinder 11. Transparent wall element 13 having surfaces 14,15 is disposed diametrically of cylinder 11 as shown in FIG. 1 such that surface 15 includes a flat portion containing axis O and together with floor 12 and inner surface 16a of semicylindrical portion 11a of cylinder 11 defines a volume V of generally semicylindrical shape. As is shown below, refractive index measurements using cell 10 of the invention is independent of the refractive indices of the material(s) comprising cylinder 11 or wall element 13. Element 13, cylinder 11 and floor 12 are appropriately sealed to each other in conventional fashion at respective lines of juncture in order to contain a liquid within volume V. It may be noted at this point that cell 10 may be constructed in generally semicylindrical shape, such as defined by wall element 13 and inner surface 16a of portion 11a of cylinder 11 shown in FIGS. 1,2 defining volume V; this will be more clearly evident from the description of the operation of cell 10 presented below. A fine reference line 19 is scribed, etched or otherwise applied to surface 15 coincident with axis O.

Cylinder 11 is supported on and in preselected spaced relationship to a base 21 on the upper surface of which is defined or on which is applied a protractor 23 coaxially witb cylinder 11. Cylinder 11 may be supported in any appropriate way such as by a pair of posts 25 one shown in FIG. 1) disposed diametrically of cylinder 11 and supporting cylinder 11 with axis O perpendicular to base 21 and the plane of protractor 23. A pair of rotatable arms 26,27 are supported for rotation about axis O in respective planes parallel to protractor 23 and perpendicular to axis O. Support means (hidden in FIG. 1) such as a screw or pin is disposed on base 21 below floor 12 concentric with protractor 23 along axis O for rotatably supporting arms 26,27.

Light source 29 is mounted on arm 26 for rotation about axis O on one side of cylinder 11. Source 29 is preferably a point or vertical line source and may be in any convenient form such as a collimated light beam, laser source, or the like, or other image sources such as a needle, cross-hair, optical slit, pinhole, reticle or the like for providinq a reference siqhtinq or light beam 31 transmitted through element 13 and portion 11a of cylinder 11 as suggested in FIG. 2. Detector 33 is mounted on arm 27 for rotation therewith about axis O opposite source 29. Detector 33 may be of any convenient form consistent with source 29 selection, and may comprise a slit, telescope, peep sight, cross hair, reticle, photovoltaic device, film strip or other means for observing source 29 or detecting transmitted beam portion 35, 35' of beam 31.

Figure 2:
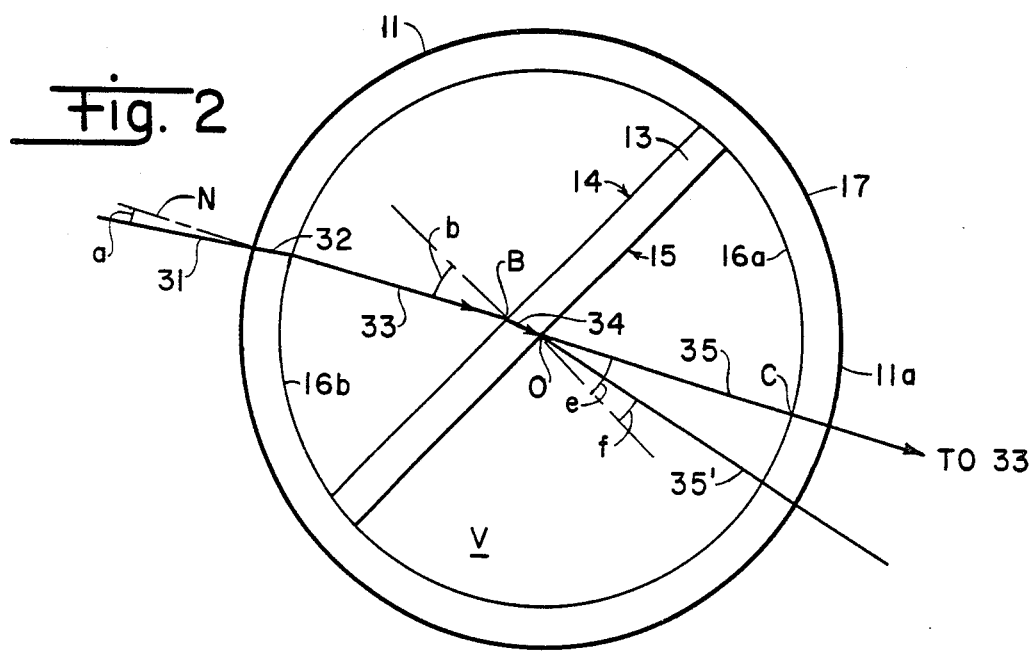
FIG. 2 is a view of the cell of FIG. 1 along line A—A.

In determining the refractive index of a liquid using cell 10, beam 31 is directed from source 29 alonq a direction as depicted in FIG. 2 through cylinder 11 At the outset. it is noted that it is critical to the operation of cell 10 that beam 31 be directed through axis O and reference line 19. If source 29 is a line source, the projected line image must coincide with reference line 19. Accordingly. in the arranqement shown in FIGS. 1, 2, beam 31 is directed at an appropriate angle a to a normal N to outer surface 17 of cylinder 11 and is refracted by cylinder 11 as shown at beam portion 32 and refracted again at inner surface 16b as shown at beam portion 33. Therefore, in order for beam 31 ultimately to pass through axis O and reference line 19, beam portion 33 does not follow a radius of cylinder 11 and impinges surface 14 of element 13 at point B and is refracted by element 13 as beam portion 34, emerging from surface 15 of element 13 at O as beam portion 35 directed along a radius toward point C. Since beam portion 35 is directed along a radius toward point C and therefore normal to surface 16a, no refraction occurs at C and beam portion 35 emerges radially outwardly toward detector 33. It is noted here that if cell 10 is semicylindrical in shape as suggested above, beam 31 may be directed at a corresponding point on surface 14 for refraction thereof by element 13 through axis O.

Consider now the angle b with respect to a normal to surface 14 at which beam portion 33 is incident at B. Geometric considerations and application of Snell's Law at B and O shows that angle b is equal to angle e between beam portion 35 and a normal to surface 15 at O where air occupies volume V, i.e., the medium on both sides of element 13 is the same. The position of detector 33 (and hence the direction of beam 35) relative to a normal to surface 15 of element 13 is determined by observing the position of arm 27 supporting detector 33 relative to protractor 23. For convenience of making a direct measurement of angle e, the component parts of cell 10 may be arranged so that prolractor 23 has a zero point coincident with an extension of a llne normal to surface 15 at O. For maximum resolution, protractor 23 and arm 27 may include electrical means for analog-to-digital conversion for electric calibration and angle recording.

Once angle e is measured, volume V is filled with a liquid the refractive index n of which is to be measured. With liquid in volume V, beam portion 34 is refracted at O along 35' at an angle f smaller than e. The index of refraction n is calculated using Snell's Law:

$$n = \frac{\sin(b)}{\sin(f)} n_{air} = \frac{\sin(e)}{\sin(f)} n_{air} \quad (1)$$

where $n_{air}$ is the index of refraction for air. Angle f is the angle of refraction for the liquid within volume V. Since $n_{air}$ is equal to 1.000 to three decimal places, the refractive index of the liquid to three decimal places is:

$$n = \sin(e)/\sin(f). \quad (2)$$

If the equipment setup permits measurement of e in vacuum, calculation of n would be absolute. Detector 33, arm 27 and protractor 23 may include means for making the calculation of Eq. (2) and providing a direct readout of n.

It is noted therefore, as postulated above, that measurements of n are independent of the refractive indices of the materials comprising cell 10. Further, it is noted that source 29 and detector 33 may be configured so that volume V may be partially filled with liquid and measurements of angles e,f made by sighting, respectively, above and below the liquid surface without otherwise altering, calibrating or adjusting cell 10 between measurements.

Cell 10 may also be used to measure the nonlinear coefficient of the refractive index of liquids. In such measurements, a laser, such as a CW or pulsed Nd:YAG, CW or pulsed Nd:Glass, pulsed argon, Excimer, CW or pulsed $CO_2$, CW or pulsed CO, pulsed ruby, dye laser or other high power type, is positioned on arm 26 as source 29, and a photovoltaic detector array, film strip, photosensitive paper, or the like is positioned on arm 27 as detector 33. The refractive index is known to behave as:

$$n = n_o + n_2(I) \quad (3)$$

where $n_o$ is the linear refractive index, I is the intensity of the laser beam and $n_2$ is the nonlinear coefficient of the refractive index. As I increases, angle f changes (decreases) and observed measurements of angle f corresponding to applied intensity I levels may be obtained using cell 10. In some cases the coefficient $n_2(I)$ is known to be negative, in which case angle f increases as a function of laser intensity.

The invention therefore provides an improved refractive index measurement cell. It is understood that certain modifications to the invention may be made as would occur to one with skill in the field of the invention. within the scope of the appended claims. All embodiments contemplated hereunder which accomplish the objects of the invention have therefore not been shown in complete detail. Other embodiments may be developed without departing from the spirit of the invention or from the scope of the appended claims.

I claim:

1. A device for measuring the refractive index of a liquid comprising:
   (a) a transparent tubular member defining a sample volume of semicylindrical shape with respect to a cylindrical axis, said tubular member being closed at one end for containing a liquid within said sample volume, said tubular member having a diametrically disposed wall element including a flat surface defining said sample volume and containing said axis;

(b) a reference line on said flat surface coincident with said axis;

(c) a light source for projecting a light beam through said wall element, reference line and sample volume, whereby said beam is refracted at said flat surface for projection through said sample volume;

(d) a detector for detecting said light beam transmitted through said sample volume;

(e) means for selectively positioning said detector about said axis; and (f) means for measuring the angular position of said detector about said axis.

2. The device of claim 1 wherein said tubular member comprises a transparent material selected from the group consisting of glass, quartz, plexiglass and plastic.

3. The device of claim 1 wherein said light source is a laser.

4. The device of claim 1 wherein said detector is one of a film strip, photosensitive paper and photovoltaic detector array.

5. A method of measuring the refractive index of a liquid comprising the steps of:

(a) providing a transparent tubular member defining a sample volume of semicylindrical shape with respect to a cylindrical axis, said tubular member being closed at one end for containing a liquid within said sample volume, said tubular member having a diametrically disposed wall element including a flat surface defining said sample volume and containing said axis and further including a reference line on said flat surface coincident with said axis;

(b) projecting a light beam through said wall element, reference line and sample volume of said tubular member, whereby said beam is refracted at said flat surface for projection through said sample volume;

(c) detecting said light beam transmitted through said sample volume;

(d) measuring the angular position of the transmitted said light beam about said axis relative to a line perpendicular to said flat surface at said reference line;

(e) inserting a liquid into said sample volume; and (f) repeating steps (b) through (d) with said liquid within said sample volume.

6. The method of claim 5 further comprising the step of determining the refractive index n of said liquid defined as the quotient of the sine of the angle measured according to step (d) without said liquid in said sample volume divided by the sine of the angle measured according to step (d) with said liquid in said sample volume.

7. The method of claim 5 wherein said tubular member comprises a material selected from the group consisting of glass, quartz, plexiglass and plastic.

* * * * *

UNITED STATES PATENT AND TRADEMARK OFFICE
CERTIFICATE OF CORRECTION

PATENT NO. : 4,756,618

DATED : July 12, 1988

INVENTOR(S) : Robert J. Spry

It is certified that error appears in the above-identified patent and that said Letters Patent is hereby corrected as shown below:

```
Column 2, line 4, after "detector", should appear a comma (,).
Column 2, line 5, after "member", should appear a comma (,).
Column 2, line 22, "drawinqs" should be ---drawings---.
Column 2, line 60, "witb" should be ---with---.
Column 2, line 61, after "25" and before "one" should appear a
right facing parenthesis, ---(---.
Column 3, line 9, "providinq" should be ---providing---.
Column 3, line 9, "siqhtinq" should be ---sighting---.
Column 3, line 20, "alonq" should be ---along---.
Column 3, line 21, after "11" should appear a period (.).
Column 3, line 22, after "outset" the period (.) should be
replaced by a comma (,).
Column 3, line 26, after "Accordingly" the period (.) should
be a comma (,).
Column 3, line 26, "arranqement" should be ---arrangement---.
Column 3, line 58, "proIractor" should be ---protractor---.
Column 3, line 59, "llne" should be ---line---.
Column 4, line 52, after "tion" the period (.) should be a
comma (,).
```

Signed and Sealed this

Twenty-ninth Day of November, 1988

*Attest:*

DONALD J. QUIGG

*Attesting Officer*  *Commissioner of Patents and Trademarks*